United States Patent [19]
Chen et al.

[11] Patent Number: 6,117,177
[45] Date of Patent: Sep. 12, 2000

[54] ARTIFICIAL KNEE JOINT HAVING A SWING PHASE CONTROL MEMBER

[75] Inventors: Sen-Jung Chen; Chien-Chuan Chen, both of Taipei, Taiwan

[73] Assignee: Teh Lin Prosthetic & Orthopaedic Inc., Taiwan

[21] Appl. No.: 09/267,801

[22] Filed: Mar. 12, 1999

[51] Int. Cl.[7] .................................. A61F 2/64; A61F 2/74
[52] U.S. Cl. ................................................. 623/44; 623/26
[58] Field of Search ................................. 623/44, 26, 24, 623/43, 39, 46

[56] References Cited

U.S. PATENT DOCUMENTS 5,904,721  5/1999  Henry et al. ............................... 623/26

Primary Examiner—David H. Willse
Attorney, Agent, or Firm—Ostrolenk, Faber, Gerb & Soffens, LLP

[57] ABSTRACT

An artificial knee joint includes a hollow cylinder (5) in which a piston member (62) is disposed movably. The piston divides the cylinder (5) into upper and lower chambers (51, 52). The swing phase control member (8) has first and second channels (80, 81), a fulcrumed lever member (82) bridging the first and second channels (80, 81). The second channel (81) is communicated with the upper and lower chambers (51, 52). The first end of the lever member (82) extends into the first channel (80) for movement in response to an air pressure in the first channel (80). The second end of the lever member (82) has a first throttle valve unit (83) for regulating the air flow through the second channel (81) in response to a movement of the lever member (82). A pump unit (7) is associated operatively with the piston member (62) for pumping air from the ambient to the first channel (80) in response to a movement of the piston member (62).

7 Claims, 6 Drawing Sheets

ARTIFICIAL KNEE JOINT HAVING A SWING PHASE CONTROL MEMBER

This invention relates to an artificial knee joint, more particularly to an artificial knee joint with a swing phase control member that enables a natural course of motion and that is in particularly suited for different fast courses of motion.

In a conventional artificial knee joint with a piston and cylinder arrangement, a swing phase control device is provided for controlling the movement of the piston into the piston and cylinder arrangement and thus the flexion of the artificial knee joint by a throttle valve. When stretching the knee joint, the person using the artificial knee joint must swing the lower leg back in first and into a position aligned with the upper leg. The throttle effect occurring in this case is the same as during the flexion. However, since flexing and stretching are separate processes, an identical throttle effect causes an unnatural course of motion. Whilst the throttle valve is adjustable and can therefore be adapted to the respective walking style, no dynamic adaptation to different courses of movement of the person is provided. Thus, the throttle valve has an optimum effect either for slow or for fast motions only.

The object of the present invention is to provide an artificial knee joint of the aforementioned kind that enables a natural course of motion and that is in particular suited for swinging and fast walking with the prosthesis.

According to the present invention, the artificial knee joint comprises:

a thigh support;

a hollow cylinder having upper and lower ends, a wall extending between the upper and lower ends, an axial bore defined by the wall and a piston member disposed movably in the axial bore, the piston member dividing the axial bore into upper and lower chambers that are adjacent respectively to the upper and lower ends of the cylinder, the wall of the cylinder having a first through-hole that is communicated with the upper chamber, and second and third through-holes that are communicated with the lower chamber;

a link assembly interconnecting pivotally the thigh support and the cylinder and joined to the piston member in the cylinder to reciprocate the piston member when the thigh support is actuated;

a swing phase control member mounted on the wall of the cylinder and having first and second channels formed therein, and a fulcrumed lever member bridging the first and second channels and having first and second ends, the second channel being communicated with the first and second through-holes in order to communicate the upper and lower chambers, the first end of the lever member extending into the first channel for movement in response to an air pressure in the first channel, the second end of the lever member carrying a first throttle valve unit for regulating a first air flow through the second channel in response to a movement of the lever member, the first channel having an outlet that opens to the ambient, the swing phase control member further having an inlet hole that is communicated with the third through-hole of the cylinder; and a pump unit associated operatively with the piston member for pumping air from the ambient to the first channel in response to a movement of the piston member via the third through-hole of the cylinder and the inlet hole of the swing phase control member so as to create the air pressure in the first channel.

Other features and advantages of the present invention will become apparent in the following detailed description of the preferred embodiments of the invention, with reference to the accompanying drawings, in which.

Before the present invention is disclosed in greater detail, it should be noted that like elements are denoted by the same reference numerals throughout the disclosure.

Figure 1:
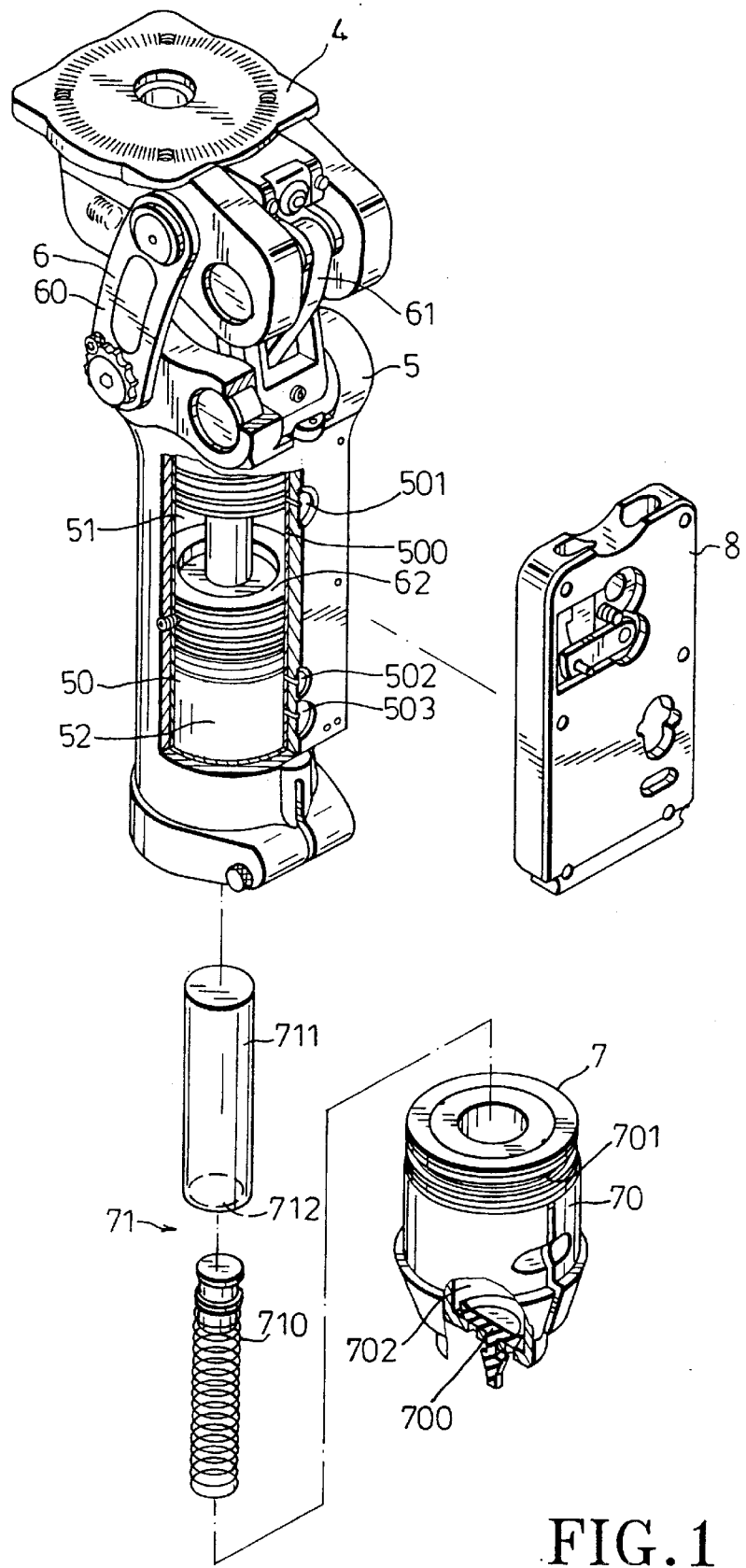
FIG. 1 is an exploded, partly sectional view of a first preferred embodiment of an artificial knee joint according to the present invention.

Referring to FIG. 1, a preferred embodiment of an artificial knee joint according to the present invention is shown to comprise a thigh support 4, a hollow cylinder 5, a link assembly 6, a pump unit 7, and a swing phase control member 8.

The hollow cylinder 5 has a tubular wall 500 extending between the upper and lower ends thereof, an axial bore 50 defined by the wall 500 and a piston member 62 disposed movably in the axial bore 50. The piston member 62 divides the axial bore 50 into upper and lower chambers 51, 52 that are adjacent respectively to the upper and lower ends of the cylinder 5. The wall 500 of the cylinder 5 has a first through-hole 501 that is communicated with the upper chamber 51, and second and third through-holes 502, 503 that are communicated with the lower chamber 52.

The link assembly 6 has a pair of linkages 60 interconnecting pivotally the thigh support 4 and the cylinder 5, and an actuating arm 61 interconnecting pivotally the piston member 62 in the cylinder 5 and the thigh support 4 so as to reciprocate the piston member 62 when the thigh support 4 is actuated.

Figure 2:
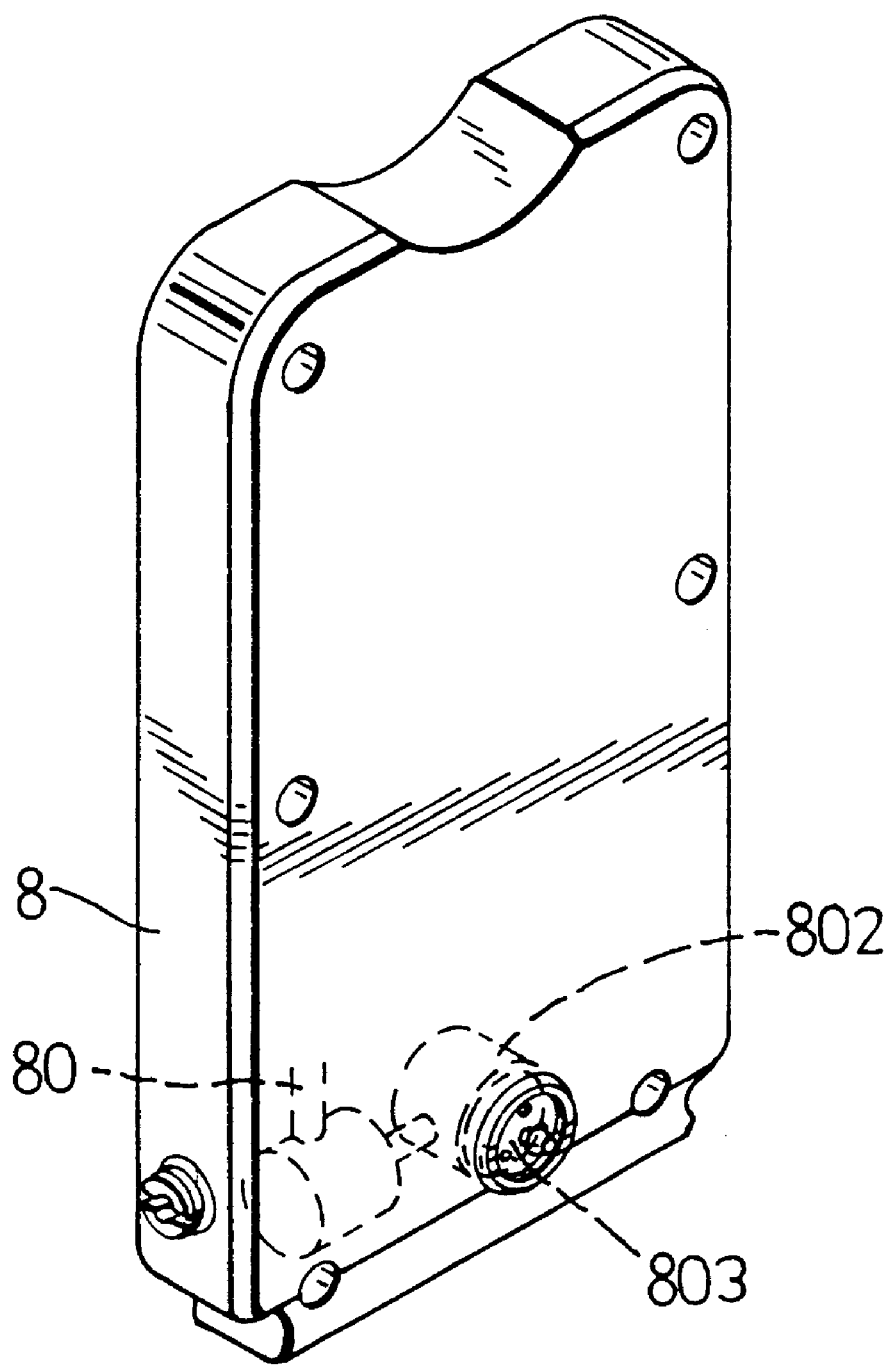
FIG. 2 is a fragmentary perspective view of a swing phase control member of the first preferred embodiment of the artificial knee joint according to the present invention.
Figure 3:
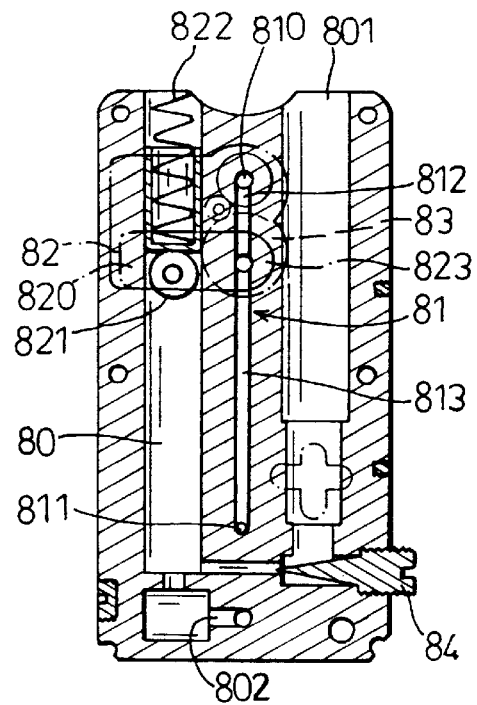
FIG. 3 is a cross-sectional view of the swing phase control member of the first preferred embodiment of the artificial knee joint according to the present invention.

Referring to FIGS. 1 and 3, the swing phase control member 8 is mounted on the wall 500 of the cylinder 5 and has a generally U-shaped first channel 80 and a linear second channel 81 formed therein, and a fulcrumed lever member 82 bridging the first and second channels 80, 81. The second channel 81 is communicated with the first and second through-holes 501, 502 via upper and lower holes 810, 811 in order to communicate the upper and lower chambers 51, 52, respectively. The lever member 82 has a first end 820 that has a stopper 821 connected thereto and that extends into the first channel 80 for movement in response to the air pressure in the first channel 80. The lever member 82 has a second end 823 carrying a first throttle valve unit 83 for regulating a first air flow through the second channel 81 in response to the movement of the lever member 82. The first channel 80 has an outlet 801 that opens to the ambient. The swing phase control member 8 further has an inlet hole 802 that is communicated with the third through-hole 503 of the cylinder 5 and the first channel 80. A check valve 803 is provided in the inlet hole 802 to prevent air from flowing from the first channel 80 to the third through-hole 503, as best illustrated in FIG. 2. The first channel 80 has a spring member 822 disposed therein to bias the stopper 821 against the air pressure in the first channel 80. The swing phase control member 8 further has a second throttle valve unit 84 disposed in the first channel 80 between the first end 820 of the lever member 82 and the outlet 801 of the first channel 80 in order to regulate a second air flow that escapes from the first channel 80 to the ambient. As such, the increasing speed of the air pressure in the first channel 80 can be controlled by the second throttle valve unit 84.

Figure 5:
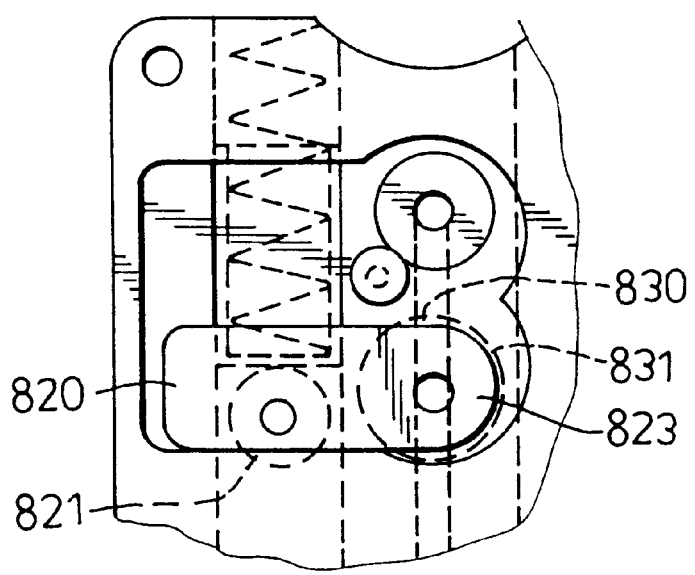
FIG. 5 is an enlarged, fragmentary schematic view illustrating a first throttle valve unit of the swing phase control member in a first operative position.

Referring to FIGS. 3 and 5, the lever member 82 is pivoted about a pivot point at the second end 823 thereof. The second channel 81 has two sections 812, 813. The first throttle valve unit 83 has a circular valve body 831 that is fixed to the second end 823 of the lever member 82 to turn about the pivot point. The valve body 831 is disposed movably between the sections 812, 813 of the second channel 81 and has a diametrical through bore 830 for intercommunicating the sections 812, 813 of the second channel 81 at varying positions. As such, the second air flow in the second channel 81 can be varied.

Referring to FIG. 1, the pump unit 7 is associated operatively with the piston member 62 for pumping air from the ambient to the first channel 80 in response to a movement of the piston member 62 via the third through-hole 503 of the cylinder 5 and the inlet hole 802 of the swing phase control member 8 so as to create the air pressure in the first channel 80. Specifically, the pump unit 7 is disposed in the lower chamber 52 of the cylinder 5, and includes a cylindrical pump casing 70 fitted into the lower end of tubular wall 500 of the cylinder 5. The pump casing 70 has an axial hole 702 extending from upper to lower ends thereof. A check valve 700 is disposed in the axial hole 702 at the lower end of the pump casing 70 to prevent air from flowing from the axial hole 702 to the ambient. A control piston 71 is disposed movably in the axial hole 702. The control piston 71 has a tube 711 with an axial blind hole 712, and a first spring member 710 that is disposed between the check valve 700 and the tube 711 and that is received partially in the axial blind hole 712 in order to bias the tube 711 to abut against the piston member 62. A vent hole 701 is formed in the pump casing 70 and interconnects the axial hole 702 and the third through-hole 503 of the cylinder 5 to permit air to be pumped from the ambient and to flow into the first channel 80 through the third through-hole 503 and the inlet hole 802 upon the movement of the piston member 62 and the control piston 71.

Figure 4:
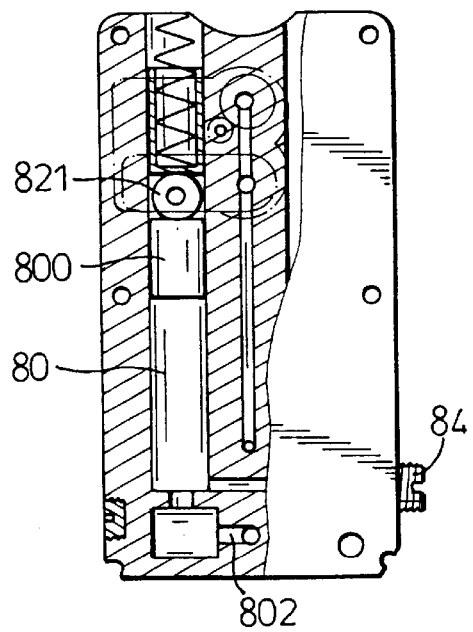
FIG. 4 is a cross-sectional view of the swing phase control member of the first preferred embodiment of the artificial knee joint according to the present invention, in which a plunger is disposed therein.

Referring to FIG. 4, a plunger 800 may be disposed in the first channel 80 between the stopper 821 and the second throttle valve unit 84. The upper end of the plunger 800 abuts against the stopper 821 when the lower end of the plunger 800 is pushed upwardly by the air pressure in the first channel 80.

Figure 6:
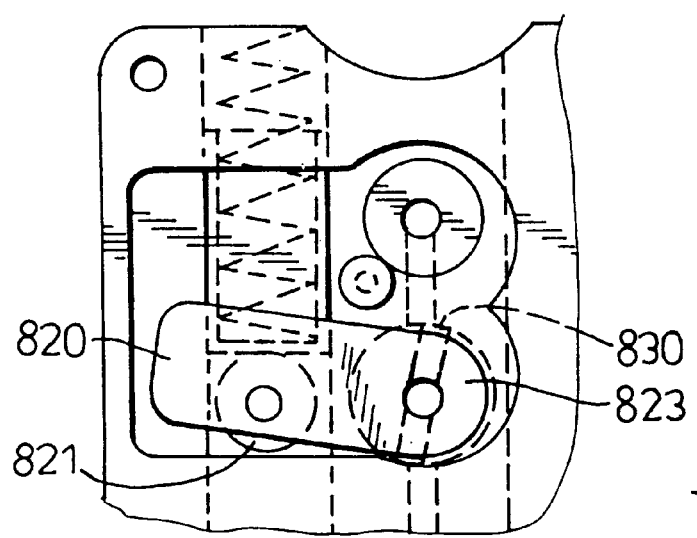
FIG. 6 is an enlarged, fragmentary schematic view illustrating the first throttle valve unit of the swing phase control member in a second operative position.

In view of the aforementioned structure, with reference to FIGS. 5 and 6, when the user's walking speed increases, the reciprocal speed of the piston member 62 and the control piston 71 is increased. Accordingly, the air pressure in the first channel 80 is quickly increased up to a high value that is sufficient to push the stopper 821 to move upwardly. The lever member 820 is then turned by an angle to turn the valve body 831 of the first throttle vale unit 83 from a first position, as shown in FIG. 5, to a second position, as shown in FIG. 6. At this time, the air flow rate per unit time flowing through the second channel 81 is reduced, thereby dampening the flexing motion and accelerating the stretching motion of the artificial knee joint. The dampening grade is determined by the axial position of the second throttle valve unit 84 or the cross-section of the throttling passage defined thereby. On the other hand, when the user wants to walk at a normal speed, he can reduce the air pressure by rotating the second throttle valve unit 84 in order to permit the air in the first channel 80 to exit quickly from the outlet 801. At this time, the spring member 822 urges the stopper 821 down to its original position, thereby resulting in the rotation of the valve body 831 of the first throttle valve unit 83 from the second position, as shown in FIG. 6, to the first position, as shown in FIG. 5. Accordingly, the air flow in the second channel 81 is increased, and the reciprocal speed of the piston member 62 is reduced to a normal value.

Figure 7:
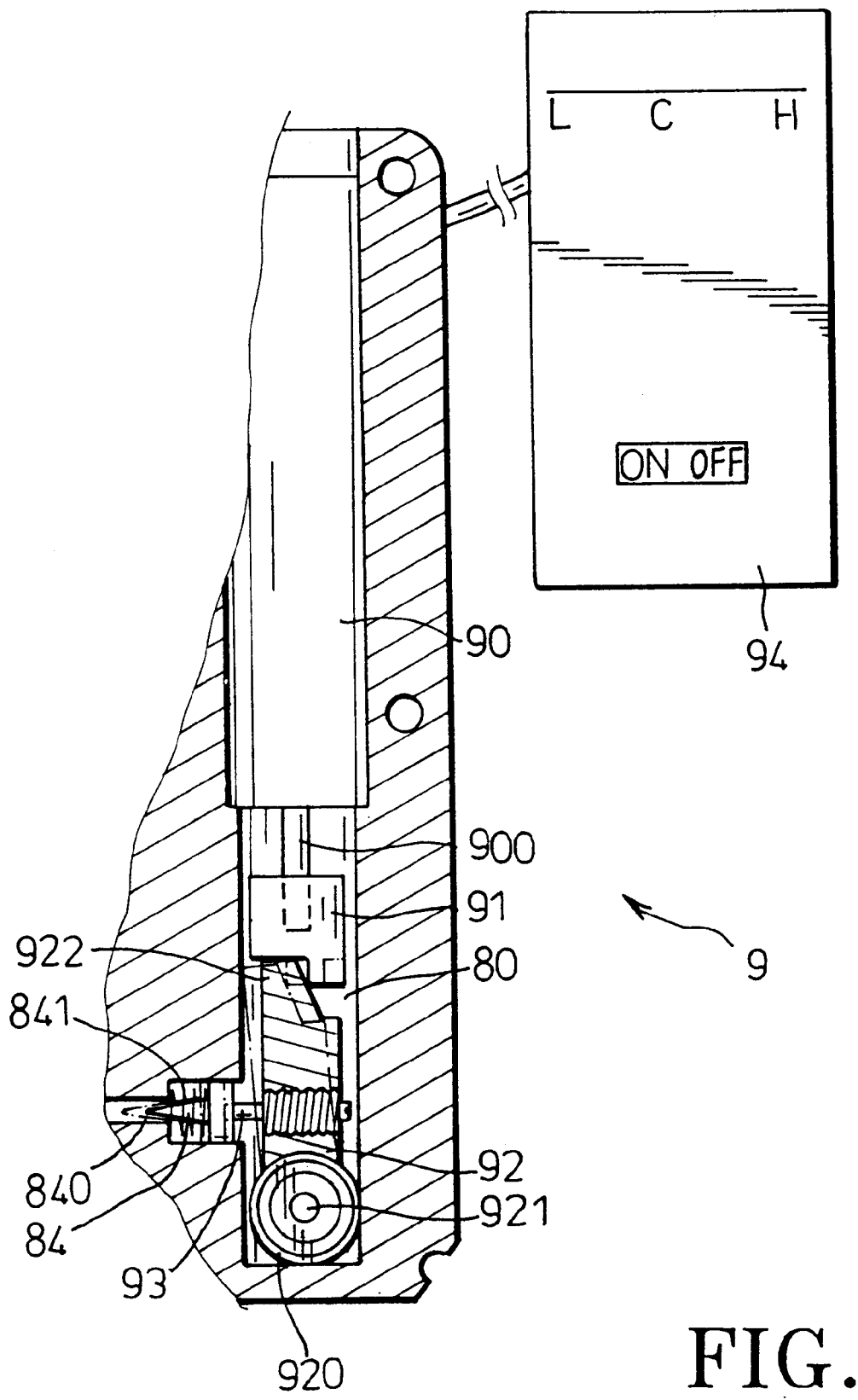
FIG. 7 is an enlarged, fragmentary view illustrating a second throttle valve unit of a second preferred embodiment of a swing phase control member and a computerized control unit associated with the second throttle valve unit.

Referring to FIG. 7, the artificial knee joint further comprises a computerized control unit 9 that is associated with the second throttle valve unit 84 so as to control the cross-section of the throttling passage 840 defined by the second throttle valve unit 84. The computerized control unit 9 includes a motor 90, an eccentric cam 91, a rotary arm 92, a rod 93, and a control panel 94. The motor 90 is disposed in the first channel 80. The eccentric cam 91 is connected to the output shaft 900 of the motor 90. The rotary arm 92 has a first end having a sleeve ring 920 that is connected to a ball bearing 921 so as to be connected pivotally in the first channel 80, and has a second end 922 that abuts against the eccentric cam 91. The second end 922 of the rotary arm 92 swings left and right when the eccentric cam 91 is rotated by the motor 90. The control panel 94 is connected electrically a microcomputer and the motor 90 in order to control the rotation speed and direction of the motor 90. When it is desired to adjust the cross-section of the throttling passage 840, the user can manipulate the control panel 94 to enable the eccentric cam 91 to turn clockwise or counterclockwise by an angle by virtue of a preset value in the microcomputer. Accordingly, the rod 93 fixed in the rotary arm 92 is then moved left or is pushed right back to its original position by a coiled spring 841.

Figure 8:
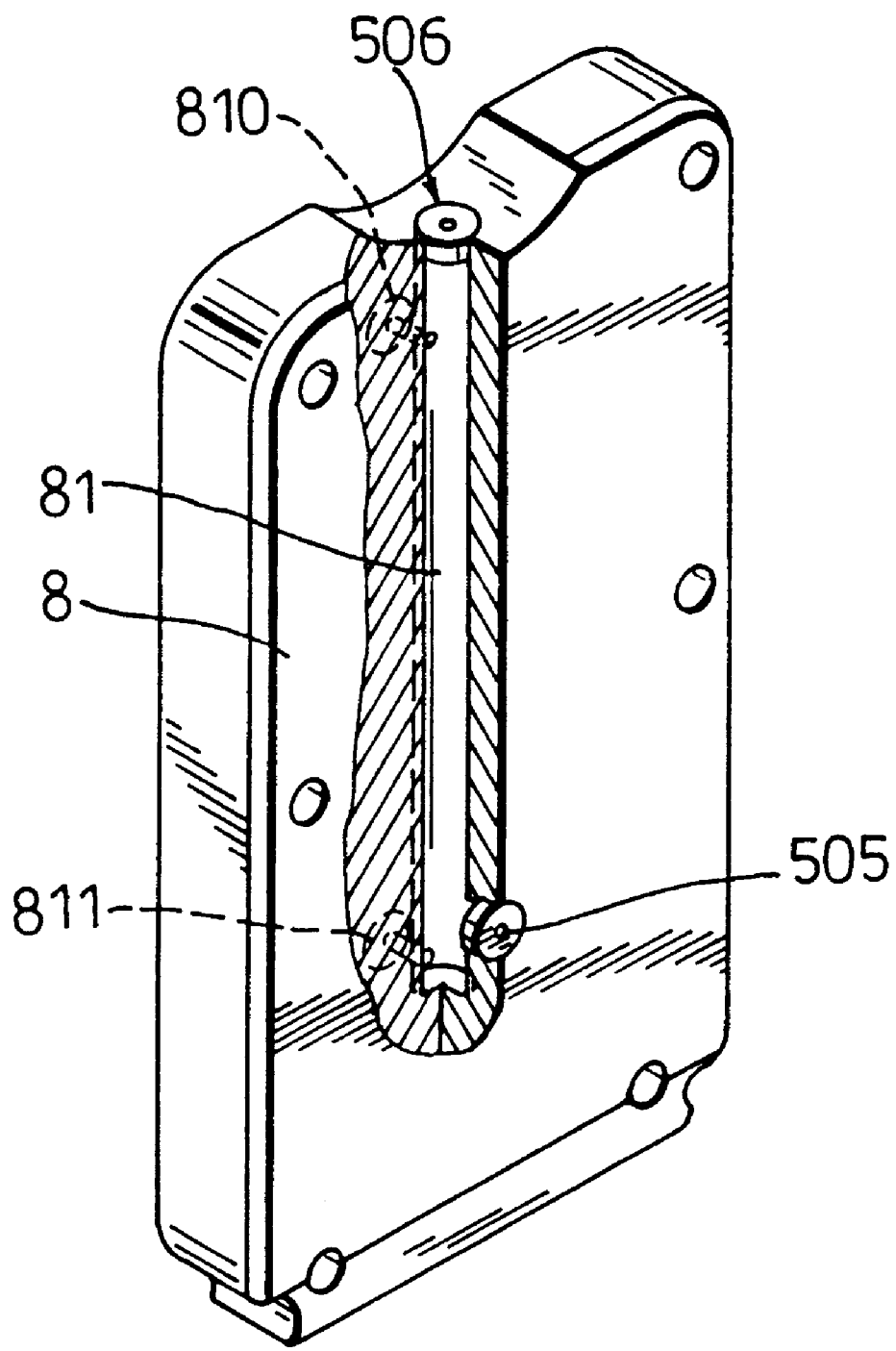
FIG. 8 is a partly sectional view illustrating a swing phase control member of a third preferred embodiment according to the present invention.

Referring to FIG. 8, the upper and lower ends of the second channel 81 may be provided respectively with an outlet check valve 506 that prevents air from flowing from the ambient to the second channel 81, and an inlet check valve 505 that prevents air from flowing from the second channel 81 to the ambient in order to avoid creation of a vacuum in the second channel 81 when the swing motion of the artificial knee joint is accelerated suddenly.

What is claimed is:

1. An artificial knee joint, comprising:
 a thigh support (4);
 a hollow cylinder (5) having upper and lower ends, a wall (500) extending between said upper and lower ends, an axial bore (50) defined by said wall (500), and a piston member (62) disposed movably in said axial bore (50), said piston member (62) dividing said axial bore (50) into upper and lower chambers (51, 52) that are adjacent respectively to said upper and lower ends of said cylinder (5), said wall (500) of said cylinder (5) having a first through-hole (501) that is communicated with said upper chamber (51), and a second through-hole (502) that is communicated with said lower chamber (52); and a link assembly (6) interconnecting pivotally said thigh support (4) and said cylinder (5) and joined to said piston member (62) in said cylinder (5) to reciprocate said piston member (62) when said thigh support (4) is actuated;

characterized by:

said wall (500) of said cylinder (5) further having a third through-hole (503) that is communicated with said lower chamber (52);

a swing phase control member (8) mounted on said wall (500) of said cylinder (5) and having first and second channels (80, 81) formed therein, and a fulcrumed lever member (82) bridging said first and second channels (80, 81) and having first and second ends (820, 823), said second channel (81) being communicated with said first and second through-holes (501, 502) in order to communicate said upper and lower chambers (51, 52), said first end (820) of said lever member (82) extending into said first channel (80) for movement in response to an air pressure in said first channel (80), said second end (823) of said lever member (82) carrying a first throttle valve unit (83) for regulating a first air flow through said second channel (81) in response to a movement of said lever member (82), said first channel (80) having an outlet (801) that opens to the ambient, said swing phase control member (8) further having an inlet hole (802) that is communicated with said third through-hole (503) of said cylinder (5); and a pump unit (7) associated operatively with said piston member (62) for pumping air from the ambient to said first channel (80) in response to a movement of said piston member (62) via said third through-hole (503) of said cylinder (5) and said inlet hole (802) of said swing phase control member (8) so as to create the air pressure in said first channel (80).

2. The artificial knee joint as claimed in claim 1, characterized in that said pump unit (7) has a pump casing (70) with upper and lower ends and fitted into said lower end of said cylinder (5), said pump casing (70) having an axial hole (702) extending from said upper end to said lower end thereof, a check valve disposed in said axial hole (702) at said lower end of said pump casing (70) to prevent air from flowing from said axial hole (702) to the ambient, a control piston (71) disposed movably in said axial hole (702), a first spring member (710) disposed between said check valve and said control piston (71) in order to bias said control piston (71) to abut against said piston member (62), and a vent hole (701) interconnecting said axial hole (702) and said third through-hole (503) of said cylinder (5) to permit air to be pumped from the ambient and to flow into said first channel (80) through said third through-hole (503) and said inlet hole (802) upon the movement of said piston member (62) and said control piston (71).

3. The artificial knee joint as claimed in claim 2, characterized in that said swing phase control member (8) further has a second throttle valve unit (84) disposed in said first channel (80) between said first end (820) of said lever member (82) and said outlet (801) of said first channel (80) in order to regulate a second air flow that escapes from said first channel (80) to the ambient.

4. The artificial knee joint as claimed in claim 3, characterized in that said first end (820) of said lever member (82) has a stopper (821) connected thereto, said first channel (80) having a second spring member (822) disposed therein to bias said stopper (821) against the air pressure in said first channel (80).

5. The artificial knee joint as claimed in claim 4, characterized in that said first channel (80) has a plunger (800) disposed movably therein between said stopper (821) and said second throttle valve unit (84).

6. The artificial knee joint as claimed in claim 4, characterized in that said lever member (82) is pivoted about a pivot point at said second end (823) of said lever member (82), said second channel (81) having two sections (812, 813), said first throttle valve unit (83) having a valve body (831) that is fixed to said second end (823) of said lever member (82) to turn about said pivot point, said valve body (831) being disposed movably between said sections (812, 813) of said second channel (81) and having a diametrical through bore (830) for intercommunicating said sections (812, 813) of said second channel (81) at varying positions.

7. The artificial knee joint as claimed in claim 3, further comprising a computerized control unit (9) that is associated with said second throttle valve unit (84) so as to control said second throttle valve unit (84).

* * * * *